US010196927B2

(12) United States Patent
Diwinsky et al.

(10) Patent No.: US 10,196,927 B2
(45) Date of Patent: *Feb. 5, 2019

(54) SYSTEM AND METHOD FOR LOCATING A PROBE WITHIN A GAS TURBINE ENGINE

(71) Applicant: General Electric Company, Schenectady, NY (US)

(72) Inventors: David Scott Diwinsky, West Chester, OH (US); Ser Nam Lim, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/041,160

(22) Filed: Feb. 11, 2016

(65) Prior Publication Data

US 2017/0167289 A1    Jun. 15, 2017

Related U.S. Application Data

(63) Continuation of application No. 14/963,695, filed on Dec. 9, 2015.

(51) Int. Cl.
F01D 17/02    (2006.01)
F01D 21/00    (2006.01)
(Continued)

(52) U.S. Cl.
CPC .......... *F01D 21/003* (2013.01); *F01D 5/005* (2013.01); *F01D 17/02* (2013.01); *G01N 21/954* (2013.01);
(Continued)

(58) Field of Classification Search
CPC ........ F01D 17/02; F01D 21/003; F01D 5/005; F05D 2270/80; F05D 2270/804;
(Continued)

(56) References Cited

U.S. PATENT DOCUMENTS 4,742,357 A * 5/1988 Rackley ................. G01S 5/04
340/539.32
5,850,469 A * 12/1998 Martin ................. G01S 5/163
345/420
(Continued)

FOREIGN PATENT DOCUMENTS

EP    2 833 187 A1    2/2015
EP    2 833 190 A1    2/2015
(Continued)

OTHER PUBLICATIONS

English language machine translation for Japanese Foreign Patent Doc. JP 2005338551 A (Kobayashi [2005]), provided from Espacenet (https://worldwide.espacenet.com/), retrieved Mar. 8, 2018. (Note a copy of JP 2005338551 A, with an English Language Abstract, was provided by Applicant with the Feb. 17, 2018 IDS filing).*
(Continued)

*Primary Examiner* — William H Rodriguez
*Assistant Examiner* — Jason H Duger
(74) *Attorney, Agent, or Firm* — General Electric Company; Brian Overbeck

(57) ABSTRACT

A method for locating probes within a gas turbine engine may generally include positioning a plurality of location transmitters relative to the engine and inserting a probe through an access port of the engine, wherein the probe includes a probe tip and a location signal receiver configured to receive location-related signals transmitted from the location transmitters. The method may also include determining a current location of the probe tip within the engine based at least in part on the location-related signals and identifying a virtual location of the probe tip within a three-dimensional model of the engine corresponding to the current location of the probe tip within the engine. Moreover, the method may include providing for display the three-dimensional model of the engine, wherein the virtual location of the probe tip is
(Continued)

displayed as a visual indicator within the three-dimensional model.

19 Claims, 7 Drawing Sheets

(51) Int. Cl.
  *G02B 23/24* (2006.01)
  *F01D 5/00* (2006.01)
  *G01N 21/95* (2006.01)
  *G01N 21/954* (2006.01)

(52) U.S. Cl.
  CPC ..... *G01N 21/9515* (2013.01); *G02B 23/2461* (2013.01); *G02B 23/2476* (2013.01); *G02B 23/2484* (2013.01); *F05D 2270/80* (2013.01); *F05D 2270/804* (2013.01)

(58) Field of Classification Search
  CPC ........ F05D 2270/8041; F05D 2220/32; G01M 15/04; G01M 15/14; G02B 23/24; G02B 23/26; G02B 23/2476; G02B 23/2484; G02B 23/2461; G01N 21/954; G01N 21/9515; G01R 33/0322; F23R 2900/0019; F23R 2900/00019; G01B 11/24; G01B 11/30
  See application file for complete search history.

(56) References Cited

U.S. PATENT DOCUMENTS

| | | | |
|---|---|---|---|
| 6,542,230 B1* | 4/2003 | Luke | B23K 26/032 356/241.1 |
| 7,064,811 B2* | 6/2006 | Twerdochlib | F01D 21/003 356/23 |
| 7,171,279 B2 | 1/2007 | Buckingham et al. | |
| 7,782,046 B2* | 8/2010 | Anderson | G01B 7/004 324/207.15 |
| 7,901,348 B2 | 3/2011 | Soper et al. | |
| 8,311,738 B2 | 11/2012 | Politick et al. | |
| 8,485,038 B2 | 7/2013 | Sengupta et al. | |
| 8,544,279 B2* | 10/2013 | Sappey | F01D 21/003 431/75 |
| 8,950,004 B2 | 2/2015 | Messinger et al. | |
| 9,026,247 B2 | 5/2015 | White et al. | |
| 9,036,892 B2 | 5/2015 | Domke et al. | |
| 2005/0199832 A1* | 9/2005 | Twerdochlib | F01D 5/005 250/559.29 |
| 2006/0025668 A1* | 2/2006 | Peterson | A61B 5/06 600/407 |
| 2006/0247511 A1* | 11/2006 | Anderson | A61B 5/06 600/407 |
| 2007/0132840 A1 | 6/2007 | Konomura | |
| 2007/0226258 A1 | 9/2007 | Lambdin et al. | |
| 2008/0186018 A1* | 8/2008 | Anderson | G01B 7/004 324/207.11 |
| 2008/0238413 A1* | 10/2008 | Anderson | G01B 7/003 324/207.17 |
| 2009/0079426 A1* | 3/2009 | Anderson | G01R 31/31709 324/301 |
| 2009/0096443 A1* | 4/2009 | Anderson | G01R 33/00 324/207.17 |
| 2009/0118620 A1* | 5/2009 | Tgavalekos | A61B 5/06 600/463 |
| 2010/0113917 A1* | 5/2010 | Anderson | A61B 5/061 600/424 |
| 2012/0203067 A1 | 8/2012 | Higgins et al. | |
| 2013/0113915 A1 | 5/2013 | Scheid et al. | |
| 2014/0098091 A1 | 4/2014 | Hori | |
| 2014/0139831 A1 | 5/2014 | Gutschow et al. | |
| 2014/0207419 A1* | 7/2014 | Messinger | G01N 27/90 703/1 |
| 2015/0172567 A1 | 6/2015 | Ekeroth | |
| 2015/0341600 A1* | 11/2015 | Hatcher, Jr. | H04N 7/183 348/82 |

FOREIGN PATENT DOCUMENTS

| | | |
|---|---|---|
| JP | H09-028659 A | 2/1997 |
| JP | 2003028947 A | 1/2003 |
| JP | 2005-338551 A | 12/2005 |
| JP | 2007-163723 A | 6/2007 |
| JP | 2009-530037 A | 8/2009 |
| WO | 2011/149582 A1 | 12/2011 |

OTHER PUBLICATIONS

Extended European Search Report and Opinion issued in connection with corresponding EP Application No. 16201971.5 dated Apr. 4, 2017.

Machine Translation and Notification of Reasons for Refusal issued in connection with corresponding JP Application No. 2016-231924 on Dec. 26, 2017.

* cited by examiner

SYSTEM AND METHOD FOR LOCATING A PROBE WITHIN A GAS TURBINE ENGINE

CROSS-REFERENCE TO RELATED APPLICATIONS

This application claims priority to and is a continuation of U.S. patent application Ser. No. 14/963,695 filed on Dec. 9, 2015 and entitled "System and Method for Locating a Probe within a Gas Turbine Engine," the disclosure of which is hereby incorporated by reference herein in its entirety for all purposes.

FIELD OF THE INVENTION

The present subject matter relates generally to gas turbine engines and, more particularly, to a system and method for locating a probe within a gas turbine engine.

BACKGROUND OF THE INVENTION

A gas turbine engine typically includes a turbomachinery core having a high pressure compressor, combustor, and high pressure turbine in serial flow relationship. The core is operable in a known manner to generate a primary gas flow. The high pressure compressor includes annular arrays ("rows") of stationary vanes that direct air entering the engine into downstream, rotating blades of the compressor. Collectively one row of compressor vanes and one row of compressor blades make up a "stage" of the compressor. Similarly, the high pressure turbine includes annular rows of stationary nozzle vanes that direct the gases exiting the combustor into downstream, rotating blades of the turbine. Collectively one row of nozzle vanes and one row of turbine blades make up a "stage" of the turbine. Typically, both the compressor and turbine include a plurality of successive stages.

In order to allow for periodic inspection of the core parts of the engine (e.g., the compressor blades and the turbine blades), borescope ports are typically provided in the engine casings and/or frames. Such ports allow optical borescope instruments to be inserted into the core engine to enable a visual inspection of the engine to be performed without requiring disassembly of the engine components. However, once an instrument has been inserted into a borescope port, minimal information is typically available to an inspector regarding the actual position of the instrument within the engine, leading to errors in measurements and reducing the efficiency of performing the visual inspection.

Accordingly, a system and method for locating a probe relative to a gas turbine engine as such probe is being inserted within the engine would be welcomed within the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a method for locating probes within a gas turbine engine. The method may generally include positioning a plurality of location transmitters relative to the gas turbine engine, wherein each location transmitter has a known location relative to the gas turbine engine. The method may also include inserting a probe through an access port of the gas turbine engine, wherein the probe includes a probe tip and a location signal receiver configured to receive location-related signals transmitted from the location transmitters. In addition, the method may include receiving the location-related signals at a computing device communicatively coupled to the probe, determining, by the computing device, a current location of the probe tip within the gas turbine engine based on the location-related signals and the known locations of the location transmitters and identifying, with the computing device, a virtual location of the probe tip within a three-dimensional model of the gas turbine engine corresponding to the current location of the probe tip within the gas turbine engine. Moreover, the method may include providing for display, by the computing device, the three-dimensional model of the gas turbine engine, wherein the virtual location of the probe tip is displayed as a visual indicator within the three-dimensional model.

In another aspect, the present subject matter is directed to a system for locating probes within a gas turbine engine. The system may generally include a plurality of location transmitters, wherein each location transmitter is positioned at a known location relative to the gas turbine engine. The system may also include a probe configured to be inserted through an access port of the gas turbine engine. The probe may include a probe tip and a location signal receiver configured to receive location-related signals transmitted from the location transmitters. In addition, the system may include a computing device communicatively coupled to the probe. The computing device may be configured to determine a current location of the probe tip within the gas turbine engine based on the location-related signals received by the location signal receiver and the known locations of the plurality of location transmitters. Moreover, the computing device may be configured to identify a virtual location of the probe tip within a three-dimensional model of the gas turbine engine corresponding to the current location of the probe tip within the gas turbine engine and provide for display the three-dimensional model of the gas turbine engine, wherein the virtual location of the probe tip is displayed as a visual indicator within the three-dimensional model.

These and other features, aspects and advantages of the present invention will be better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
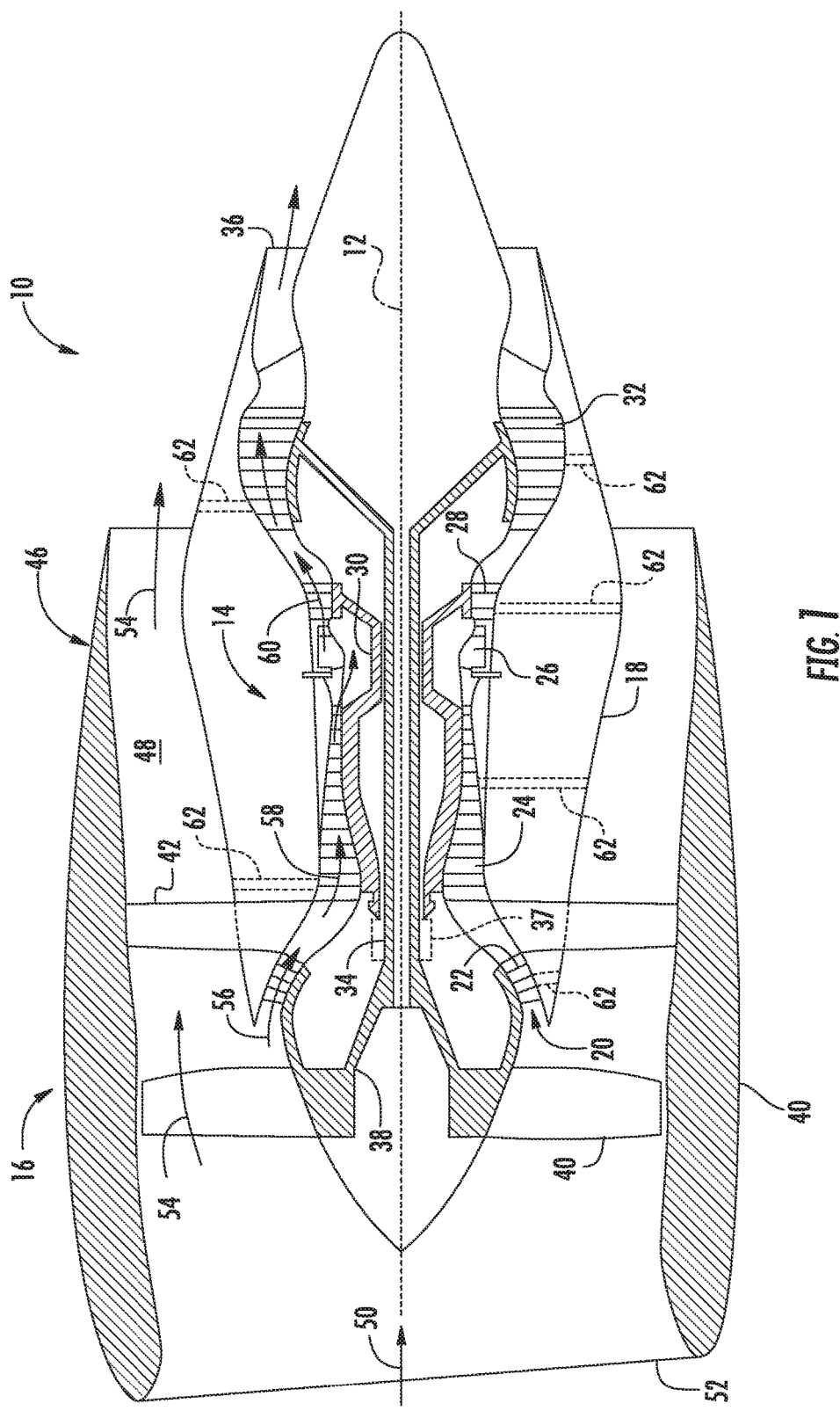
FIG. 1 illustrates a cross-sectional view of one embodiment of a gas turbine engine that may be utilized within an aircraft in accordance with aspects of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a system and method for locating a probe within a gas turbine engine. Specifically, in several embodiments, an optical probe used to visually inspect a gas turbine engine may be equipped with a suitable receiver configured to receive location-related signals from a plurality of location transmitters installed relative to the engine (e.g., within access ports of the engine). The location-related signals received by the probe receiver may then be transmitted to a computing device configured to determine the current location of the optical probe within the gas turbine engine, such as by using a trilateration or a triangulation technique to calculate the location of the probe based on the location-related signals and the known locations of the transmitters. In addition, the computing device may be configured to correlate the determined real-world location of the optical probe to a virtual location within a three-dimensional model of the gas turbine engine. The three-dimensional model may then be presented to a user of the system with the current location of the optical probe being displayed within the model (e.g., as a symbol or other visual indicator), which may allow the user to more accurately position the probe within the gas turbine engine as a visual inspection of the engine is being performed. In addition, by determining the location of the optical probe within the engine, the computing device may also be configured to identify the internal component(s) located adjacent to the probe tip. The name(s) and/or reference number(s) of the adjacent internal component(s) may then be presented to the user of the system along with the current location of the optical probe.

It should be appreciated that, although the present subject matter will generally be described herein with reference to determining the location of an optical probe within a gas turbine engine, the disclosed system and method may be generally used to determine the location of any probe inserted within a gas turbine engine. For instance, the system and method may be used to determine the location of a repair probe that has been inserted within a gas turbine engine via one of its access ports to allow for a given repair procedure to be performed within the engine.

It should also be appreciated that the disclosed system and method may generally be used to locate probes inserted within any suitable type of gas turbine engine, including aircraft-based turbine engines and land-based turbine engines, regardless of the engine's current assembly state (e.g., fully or partially assembled). Additionally, with reference to aircraft engines, it should be appreciated that the present subject matter may be used on wing or off wing.

Referring now to the drawings, FIG. 1 illustrates a cross-sectional view of one embodiment of a gas turbine engine 10 that may be utilized within an aircraft in accordance with aspects of the present subject matter, with the engine 10 being shown having a longitudinal or axial centerline axis 12 extending therethrough for reference purposes. In general, the engine 10 may include a core gas turbine engine (indicated generally by reference character 14) and a fan section 16 positioned upstream thereof. The core engine 14 may generally include a substantially tubular outer casing 18 that defines an annular inlet 20. In addition, the outer casing 18 may further enclose and support a booster compressor 22 for increasing the pressure of the air that enters the core engine 14 to a first pressure level. A high pressure, multi-stage, axial-flow compressor 24 may then receive the pressurized air from the booster compressor 22 and further increase the pressure of such air. The pressurized air exiting the high-pressure compressor 24 may then flow to a combustor 26 within which fuel is injected into the flow of pressurized air, with the resulting mixture being combusted within the combustor 26. The high energy combustion products are directed from the combustor 26 along the hot gas path of the engine 10 to a first (high pressure) turbine 28 for driving the high pressure compressor 24 via a first (high pressure) drive shaft 30, and then to a second (low pressure) turbine 32 for driving the booster compressor 22 and fan section 16 via a second (low pressure) drive shaft 34 that is generally coaxial with first drive shaft 30. After driving each of turbines 28 and 32, the combustion products may be expelled from the core engine 14 via an exhaust nozzle 36 to provide propulsive jet thrust.

Additionally, as shown in FIG. 1, the fan section 16 of the engine 10 may generally include a rotatable, axial-flow fan rotor assembly 38 that is configured to be surrounded by an annular fan casing 40. It should be appreciated by those of ordinary skill in the art that the fan casing 40 may be configured to be supported relative to the core engine 14 by a plurality of substantially radially-extending, circumferentially-spaced outlet guide vanes 42. As such, the fan casing 40 may enclose the fan rotor assembly 38 and its corresponding fan rotor blades 44. Moreover, a downstream section 46 of the fan casing 40 may extend over an outer portion of the core engine 14 so as to define a secondary, or by-pass, airflow conduit 48 that provides additional propulsive jet thrust.

It should be appreciated that, in several embodiments, the second (low pressure) drive shaft 34 may be directly coupled to the fan rotor assembly 38 to provide a direct-drive configuration. Alternatively, the second drive shaft 34 may be coupled to the fan rotor assembly 38 via a speed reduction device 37 (e.g., a reduction gear or gearbox) to provide an indirect-drive or geared drive configuration. Such a speed reduction device(s) may also be provided between any other suitable shafts and/or spools within the engine 10 as desired or required.

During operation of the engine 10, it should be appreciated that an initial air flow (indicated by arrow 50) may enter the engine 10 through an associated inlet 52 of the fan casing 40. The air flow 50 then passes through the fan blades 44 and splits into a first compressed air flow (indicated by arrow 54) that moves through conduit 48 and a second compressed air flow (indicated by arrow 56) which enters the booster compressor 22. The pressure of the second compressed air flow 56 is then increased and enters the high pressure compressor 24 (as indicated by arrow 58). After mixing with fuel and being combusted within the combustor 26, the combustion products 60 exit the combustor 26 and flow through the first turbine 28. Thereafter, the combustion products 60 flow through the second turbine 32 and exit the exhaust nozzle 36 to provide thrust for the engine 10.

The gas turbine engine 10 may also include a plurality of access ports defined through its casings and/or frames for providing access to the interior of the core engine 14. For instance, as shown in FIG. 1, the engine 10 may include a plurality of access ports 62 (only six of which are shown) defined through the outer casing 18 for providing internal access to one or both of the compressors 22, 24 and/or for providing internal access to one or both of the turbines 28, 32. In several embodiments, the access ports 62 may be spaced apart axially along the core engine 14. For instance, the access ports 62 may be spaced apart axially along each compressor 22, 24 and/or each turbine 28, 32 such that at least one access port 62 is located at each compressor stage and/or each turbine stage for providing access to the internal components located at such stage(s). In addition, the access ports 62 may also be spaced apart circumferentially around the core engine 14. For instance, a plurality of access ports 62 may be spaced apart circumferentially around each compressor stage and/or turbine stage.

It should be appreciated that, although the access ports 62 are generally described herein with reference to providing internal access to one or both of the compressors 22, 24 and/or for providing internal access to one or both of the turbines 28, 32, the gas turbine engine 10 may include access ports 62 providing access to any suitable internal location of the engine 10, such as by including access ports 62 that provide access within the combustor 26 and/or any other suitable component of the engine 10.

Figure 2:
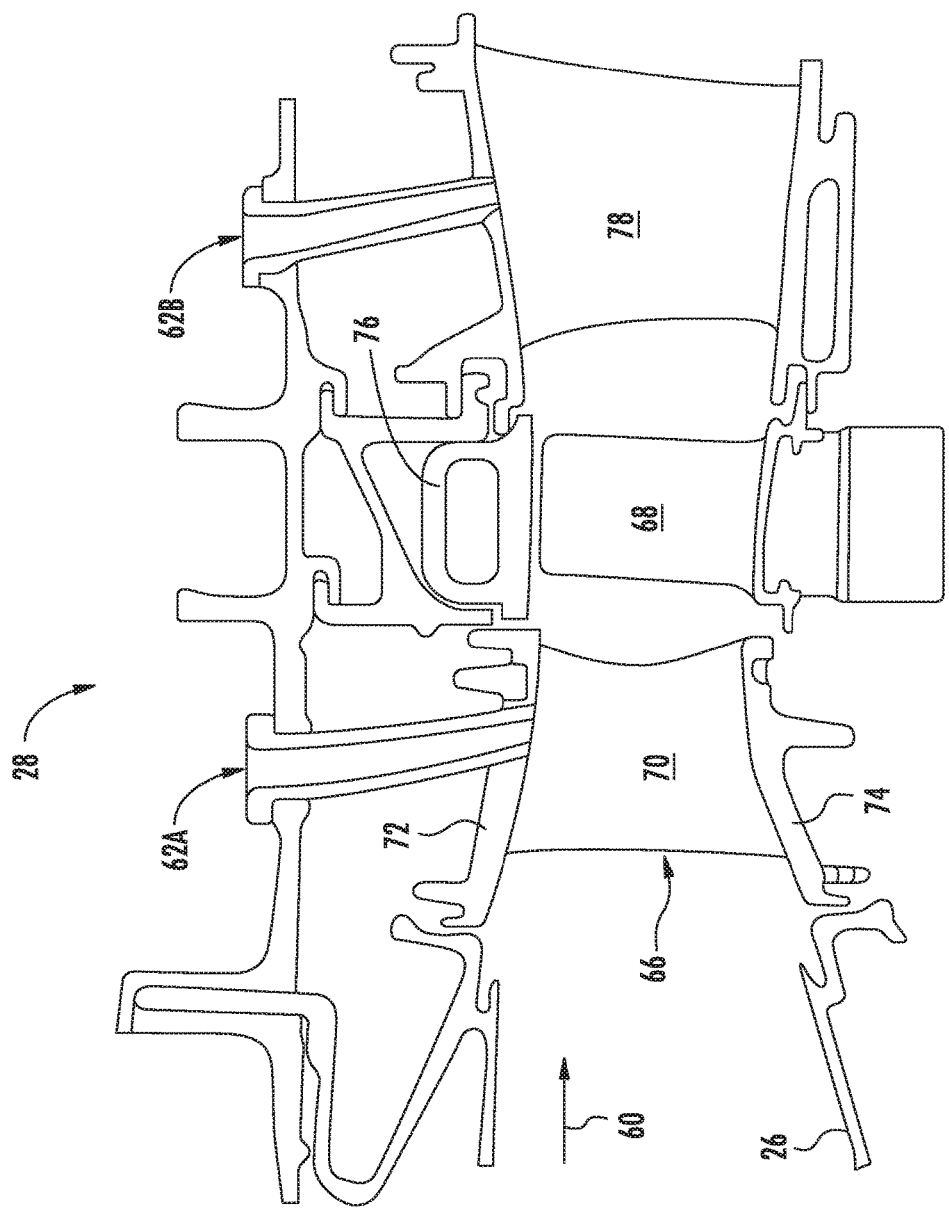
FIG. 2 illustrates a partial, cross-sectional view of one embodiment of a turbine suitable for use within the gas turbine engine shown in FIG. 1, particularly illustrating access ports defined in the engine for providing internal access to the turbine.

Referring now to FIG. 2, a partial, cross-sectional view of the first (or high pressure) turbine 28 described above with reference to FIG. 1 is illustrated in accordance with embodiments of the present subject matter. As shown, the first turbine 28 may include a first stage turbine nozzle 66 and an annular array of rotating turbine blades 68 (one of which is shown) located immediately downstream of the nozzle 66. The nozzle 66 may generally be defined by an annular flow channel that includes a plurality of radially-extending, circularly-spaced nozzle vanes 70 (one of which is shown). The vanes 70 may be supported between a number of arcuate outer bands 72 and arcuate inner bands 74. Additionally, the circumferentially spaced turbine blades 68 may generally be configured to extend radially outwardly from a rotor disk (not shown) that rotates about the centerline axis 12 (FIG. 1) of the engine 10. Moreover, a turbine shroud 76 may be positioned immediately adjacent to the radially outer tips of the turbine blades 68 so as to define the outer radial flowpath boundary for the combustion products 60 flowing through the turbine 28 along the hot gas path of the engine 10.

As indicated above, the turbine 28 may generally include any number of turbine stages, with each stage including an annular array of nozzle vanes and follow-up turbine blades 68. For example, as shown in FIG. 2, an annular array of nozzle vanes 78 of a second stage of the turbine 28 may be located immediately downstream of the turbine blades 68 of the first stage of the turbine 28.

Moreover, as shown in FIG. 2, a plurality of access ports 62 may be defined through the turbine casing and/or frame, with each access port 62 being configured to provide access to the interior of the turbine 28 at a different axial location. Specifically, as indicated above, the access ports 62 may, in several embodiments, be spaced apart axially such that each access port 62 is aligned with or otherwise provides interior access to a different stage of the turbine 28. For instance, as shown in FIG. 2, a first access port 62A may be defined through the turbine casing/frame to provide access to the first stage of the turbine 28 while a second access port 62B may be defined through the turbine casing/frame to provide access to the second stage of the turbine 28.

It should be appreciated that similar access ports 62 may also be provided for any other stages of the turbine 28 and/or for any turbine stages of the second (or low pressure) turbine 32. It should also be appreciated that, in addition to the axially spaced access ports 62 shown in FIG. 2, access ports 62 may be also provided at differing circumferentially spaced locations. For instance, in one embodiment, a plurality of circumferentially spaced access ports may be defined through the turbine casing/frame at each turbine stage to provide interior access to the turbine 28 at multiple circumferential locations around the turbine stage.

Figure 3:
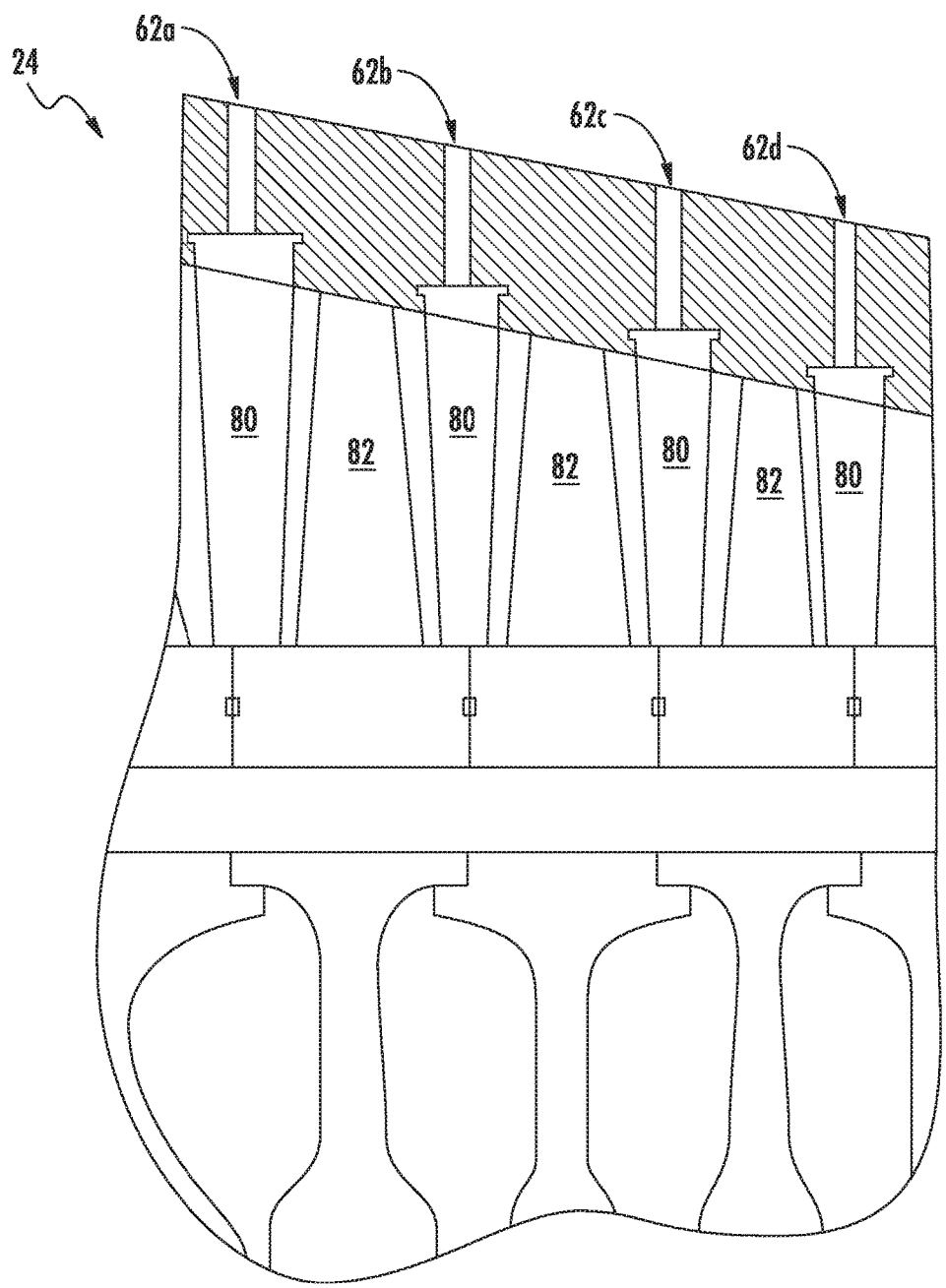
FIG. 3 illustrates a partial, cross-sectional view of one embodiment of a compressor suitable for use within the gas turbine engine shown in FIG. 1, particularly illustrating access ports defined in the engine for providing internal access to the compressor.

Referring now to FIG. 3, a partial, cross-sectional view of the high pressure compressor 24 described above with reference to FIG. 1 is illustrated in accordance with embodiments of the present subject matter. As shown, the compressor 24 may include a plurality of compressor stages, with each stage including both an annular array of fixed compressor vanes 80 (only one of which is shown for each stage) and an annular array of rotatable compressor blades 82 (only one of which is shown for each stage). Each row of compressor vanes 80 is generally configured to direct air flowing through the compressor 24 to the row of compressor blades 82 immediately downstream thereof.

Moreover, the compressor 24 may include a plurality of access ports 62 defined through the compressor casing/frame, with each access port 62 being configured to provide access to the interior of the compressor 24 at a different axial location. Specifically, in several embodiments, the access ports 62 may be spaced apart axially such that each access port 62 is aligned with or otherwise provides interior access to a different stage of the compressor 24. For instance, as shown in FIG. 3, first, second, third and fourth access ports 62a, 62b, 62c, 62d are illustrated that provide access to four successive stages, respectively, of the compressor 24.

It should be appreciated that similar access ports 62 may also be provided for any of the other stages of the compressor 24 and/or for any of the stages of the low pressure compressor 22. It should also be appreciated that, in addition to the axially spaced access ports 62 shown in FIG. 3, access ports 62 may be also provided at differing circumferentially spaced locations. For instance, in one embodiment, a plurality of circumferentially spaced access ports may be defined through the compressor casing/frame at each compressor stage to provide interior access to the compressor 24 at multiple circumferential locations around the compressor stage.

Figure 4:
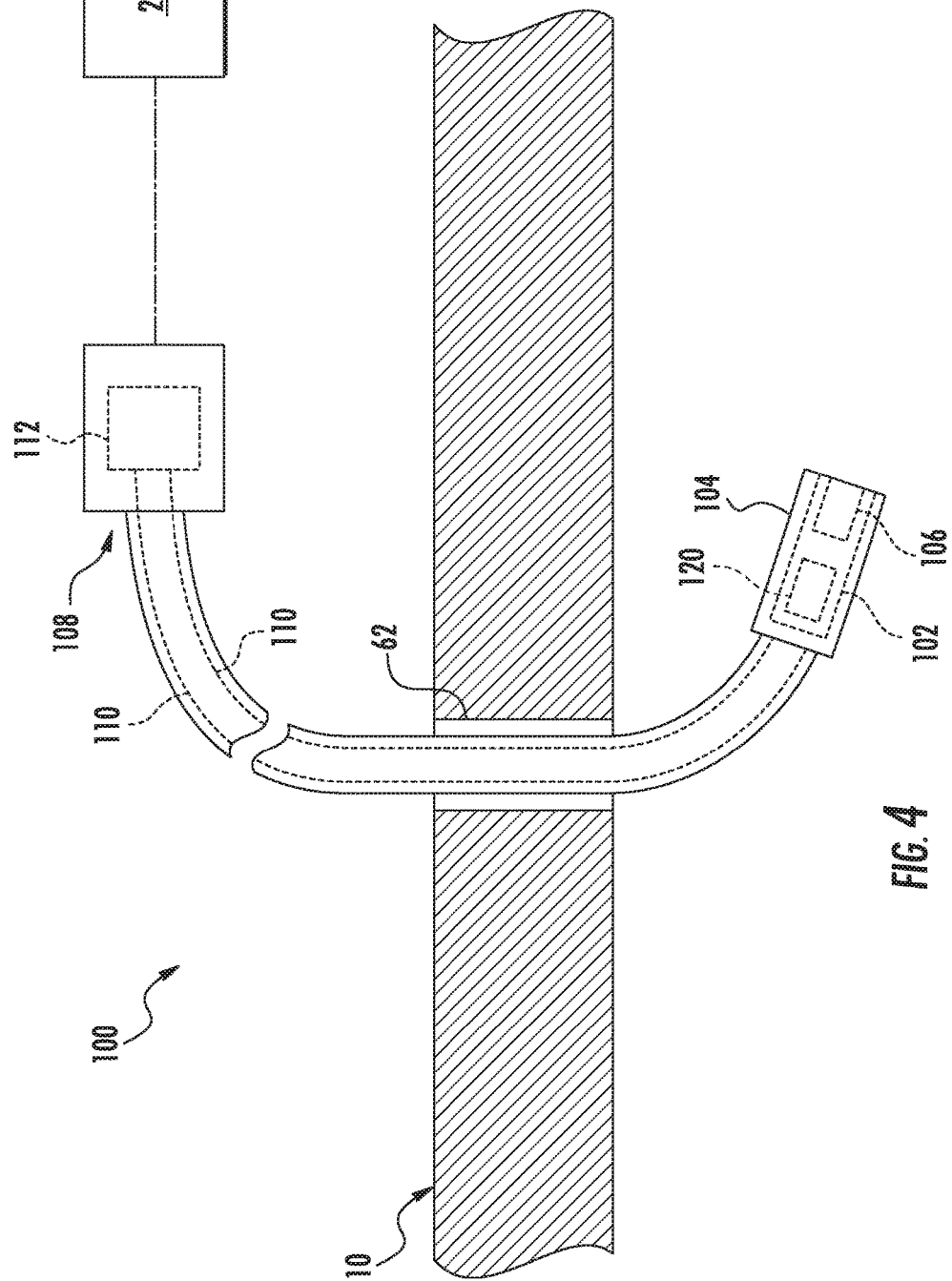
FIG. 4 illustrates a simplified view of one embodiment of an optical probe that may be used in accordance with aspects of the present subject matter to visually inspect a gas turbine engine.

Referring now to FIG. 4, a simplified view of one embodiment of a probe 100 that may be utilized to perform a visual inspection of a gas turbine engine 10 is illustrated in accordance with aspects of the present subject matter. As shown, the probe 100 has been inserted through an access port 62 of the engine 10, such as any of the access ports 62 described above with reference to FIGS. 1-3.

In general, the probe 100 may correspond to any suitable probe configured to be inserted within the gas turbine engine 10 via an access port 62. Specifically, as shown in the illustrated embodiment, the probe 100 corresponds to an optical probe 100. In such an embodiment, the optical probe 100 may correspond to any suitable optical device that may be inserted through an access port 62 of the gas turbine engine 10 to allow images of the interior of the engine 10 to be captured or otherwise obtained. For instance, in several embodiments, the optical probe 100 may correspond to a borescope, videoscope, fiberscope or any other similar optical device known in the art that allows for the interior of a gas turbine engine 10 to be viewed through an access port 62. In such embodiments, the optical probe 100 may include one or more optical elements (indicated schematically by dashed box 102), such as one or more optical lenses, optical fibers, image capture devices (e.g., video cameras, still-image cameras, CCD devices, CMOS devices), cables, and/or the like, for obtaining views or images of the interior of the engine 10 at a tip 104 of the probe 100 and for transmitting or relaying such images from the probe tip 104 along the length of the probe 100 to the exterior of the engine 10. For instance, as shown in FIG. 4, the interior views or images obtained by the probe 100 may be transmitted from the probe tip 104 to a computing device 202 connected or otherwise coupled to the probe 100. Additionally, as shown in FIG. 4, in one embodiment, a light source (indicated by dashed box 106), such as an LED, may be provided at or adjacent to the probe tip 104 to provide lighting within the interior of the engine 10.

The optical probe 100 may also include an articulation assembly 108 that allows the orientation of the probe tip 104 to be adjusted within the interior of the gas turbine engine 10. For example, the articulation assembly 108 may allow for the probe tip 104 to be rotated or pivoted about a single axis or multiples axes to adjust the orientation of the tip 104 relative to the remainder of the probe 100. It should be appreciated that the articulation assembly 108 may generally have any suitable configuration and/or may include any suitable components that allow for adjustment of the orientation of the probe tip 104 relative to the remainder of the probe 100. For example, in one embodiment, a plurality of articulation cables 110 may be coupled between the probe tip 104 and one or more articulation motors 112. In such an embodiment, by adjusting the tension of the cables 110 via the motor(s) 112, the probe tip 104 may be reoriented within the gas turbine engine 10.

It should also be appreciated that, in several embodiments, the articulation assembly 108 may be configured to be electronically controlled. Specifically, as shown in FIG. 4, the computing device 202 may be communicatively coupled to the articulation assembly 108 to allow the computing device 202 to adjust the orientation of the probe tip 104 via control of the articulation assembly 108. For instance, in the illustrated embodiment, the computing device 202 may be configured to transmit suitable control signals to the articulation motor(s) 112 in order to adjust the tension within the associated cable(s) 110, thereby allowing the computing device 202 to automatically adjust the orientation of the probe tip 104 within the gas turbine engine 10.

Additionally, as shown in FIG. 4, the optical probe 100 may also include a location signal receiver (indicated schematically by dashed box 120) positioned at or adjacent to the probe tip 104. As will be described in greater detail below, the location signal receiver 120 may be configured to receive location-related signals from a plurality of location transmitters 204 (FIG. 5) that provide an indication of the position of the location signal receiver 120 (and, thus, the probe tip 104) relative to the location transmitters 204. For instance, the location signal receiver 120 may be configured to receive signals from the location transmitters 204 that provide an indication of the distance defined between the receiver 120 and each transmitter 204 (e.g., based on the signal strength, the time of flight of the signals and/or time of arrival of the signals) and/or that provide an indication of the angle defined between the receiver 120 and each transmitter 204 (e.g., based on the angle of incidence or angle of arrival of the signals). The signals received by the location signal receiver 120 may then be transmitted to the computing device 202 to allow the computing device 202 to determine the current location of the probe tip 104 within the gas turbine engine 10 using any suitable signal-based positioning technique, such as a trilateration technique or a triangulation technique.

It should be appreciated that, in other embodiments, the probe 100 may correspond to any other suitable probe configured to be inserted within the gas turbine engine 10 via one of its access ports 62. For instance, in an alternative embodiment, the probe 100 may correspond to a repair probe configured to be inserted within the gas turbine engine 10 to allow a repair procedure to be performed on one or more of the internal engine components, such as a probe used to repair cracks and/or other damage within the engine.

Figure 5:
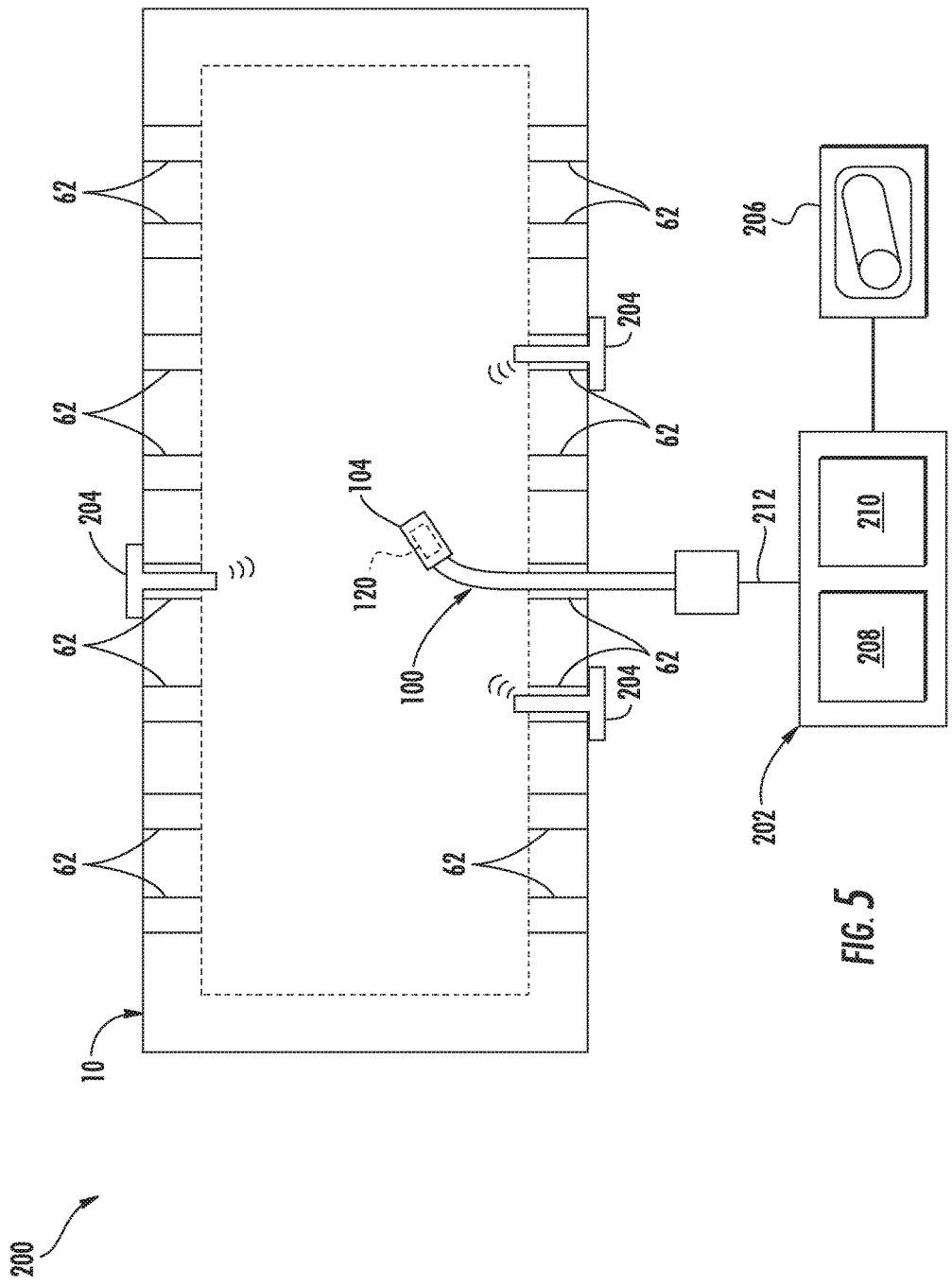
FIG. 5 illustrates a simplified, schematic view of one embodiment of a system for locating a probe within a gas turbine engine in accordance with aspects of the present subject matter.

Referring now to FIG. 5, a simplified, schematic view of one embodiment of a system 200 for locating a probe within a gas turbine engine is illustrated in accordance with aspects of the present subject matter. As shown, the system 200 may generally include a computing device 202, a probe 100 installed within an access port 62 of the gas turbine engine 10 and a plurality of location transmitters 204 positioned relative to the gas turbine engine 10. As indicated above, the probe 100 may, in several embodiments, be configured to provide an internal view or image of the gas turbine engine 10, which may then be transmitted to the computing device 202 as image data for subsequent storage thereon and/or for presentation to a user of the system 200 via a display device 206 associated with the computing device 202. Additionally, as the probe 100 is being used to obtain internal images of the gas turbine engine 10, the probe 100 may also be configured to receive location-related signals (e.g., via its location signal receiver 120) transmitted from the location transmitters 204 that provide an indication of the position of each transmitter 204 relative to the probe 100. As described above, such signals may then be transmitted to the computing device 202 to allow the computing device 202 to determine the current three-dimensional location of the probe tip 104 within the gas turbine engine 10. The determined real-world location of the probe tip 104 may then be displayed to the user of the system 200 (e.g., via the display device 206) at a corresponding virtual location within a three-dimensional computer-based model of the gas turbine engine 10 to provide the user with a visual indication of the current location of the probe 100 within the engine 10.

In general, the computing device 202 may correspond to any suitable processor-based device and/or any suitable combination of processor-based devices. Thus, in several embodiments, the computing device 202 may include one or more processor(s) 208 and associated memory device(s) 210 configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 210 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 210 may generally be configured to store suitable computer-readable instructions that, when implemented by the processor(s) 208, configure the computing device 202 to perform various functions including, but not limited to, determining the current location of the probe tip 104 within the gas turbine engine 10 based at least in part on the signals received from the transmitters 204 and providing for display a visual indication of the location of the probe tip 104 within a three-dimensional model of the engine 10.

As shown in FIG. 5, the computing device 202 may be communicatively coupled to the probe 100 (e.g., via a communicative link or cable 212). As such, image data associated with the internal views or images obtained by the probe 100 may be transmitted to the computing device 202. Such image data may then be used to allow the interior of the gas turbine engine 10 to be visually inspected at or adjacent to the location of the access port 62 within which the probe 100 has been inserted. For example, in one embodiment, the image data may be stored within the device's memory 210 to allow the images to be analyzed at a later time/date to identify defects and/or damage within the engine 10. In addition (or an alternative thereto), the image data may be transmitted from the computing device 202 to the associated display device 206 to allow a user of the system 200 to view the various internal images provided by the probe 100.

In addition, the connection provided between the probe 100 and the computing device 202 may also allow the location-related signals received by the location signal receiver 120 from the transmitters 204 to be transmitted to the computing device 202 for subsequent processing and/or analysis. For example, the transmitters 204 may be configured to continuously transmit location-related signals to the receiver 120 as the probe 100 is being used to visually inspect the interior of the gas turbine engine 10. Such location-related signals may then be transmitted to the computing device 202 to allow for a real-time determination to be made of the current location of the probe 100 within the engine 10.

In several embodiments, the location transmitters 204 may be configured to be installed within and/or inserted through separate access ports 62 of the gas turbine engine 10. For example, as shown in FIG. 5, the location transmitters 204 are positioned within differing access ports 62 than the access port 62 within which the probe 100 is installed. As such, the position of each location transmitter 204 relative to the gas turbine 10 may be determined or known by identifying the specific access port 62 within which each transmitter 204 is installed. Such known positions of the location transmitters 204 may then be input into and/or stored with the memory 210 of the computing device 202 for subsequent use in determining the current location of the probe tip 104 within the gas turbine engine 10. Alternatively, the location transmitters 204 may be configured to be positioned at any other suitable location relative to the gas turbine engine 10 (e.g., any suitable location on, within and/or outside of the engine 10) that allows the location-related signals generated by each transmitter 204 to be received by the location signal receiver 120 of the probe 100. In such an embodiment, based on the installation locations of the transmitters 204, the position of each location transmitter 204 relative to gas turbine engine 10 may be determined and subsequently input into and/or stored within the memory 208 of the computing device 202.

As shown in FIG. 5, the system 200 includes three location transmitters 204 positioned relative to the gas turbine engine 10 for transmitting location-related signals to the location signal receiver 120 of the probe 100. However, in other embodiments, any other suitable number of location transmitters 204 may be utilized within the system 200 assuming that a sufficient amount of transmitters 204 are providing for allowing the current location of the probe tip 104 to be determined based on the location-related signals transmitted by the transmitters 204 and the known locations of such transmitters 204.

It should be appreciated that the computing device 202 may generally be configured to determine the current location of the probe tip 104 using any suitable signal-based positioning technique known in the art. For instance, in one embodiment, the computing device 202 may be configured to utilize a trilateration technique to determine the current location of the probe tip 104. In such an embodiment, the computing device 202 may be configured to determine the distance defined between each location transmitter 204 and the probe tip 104 based on the location-related signals received at the location signal receiver 120. For instance, the distance between each location transmitter 204 and the probe tip 104 may be determined based on the signal strength of the location-related signals received at the receiver 120 from each transmitter 204 (e.g., using a received signal strength indicator (RSSI)). Alternatively, the distance may be determined based on the time of flight or time of arrival of the location-related signals received from each transmitter 204. Based on the distance defined between the probe tip 104 and each location transmitter 204, the computing device 202 may be configured to determine the three-dimensional location of the probe tip 104 relative to the transmitters 204. Thereafter, based on the known locations of the transmitters 204 relative to the gas turbine engine 10, the computing device 202 may calculate the current three-dimensional location of the probe tip 104 within the engine 10 (e.g., based on the known dimensions of the gas turbine engine 10).

In another embodiment, the computing device 202 may be configured to utilize a triangulation technique to determine the current location of the probe tip 104. In such an embodiment, the computing device 202 may be configured to determine the relative angle defined between each location transmitter 204 and the probe tip 104 based on the location-related signals received at the location signal receiver 120. For instance, the receiver 120 may include a dual-antenna array that allows the receiver 120 to detect the angle of incidence or angle of arrival of the location-related signals received from each transmitter 204. Based on the relative angle defined between the probe tip 104 and each location transmitter 204, the computing device 202 may be configured to determine the three-dimensional location of the probe tip 104 relative to the transmitters 204. Thereafter, based on the known locations of the transmitters 204 relative to the gas turbine engine 10, the computing device 202 may calculate the current three-dimensional location of the probe tip 104 within the engine 10 (e.g., based on the known dimensions of the gas turbine engine 10).

Additionally, as indicated above, the computing device 202 may also be configured to provide for display (e.g., via the display device 206) a three-dimensional model of the gas turbine engine 10 that provides a virtual representation of the current location of the probe tip 104 within the engine 10. For instance, a computer-aided design (CAD) model or other suitable computer-based three-dimensional model may be stored within the memory 210 of the computing device 202. In such an embodiment, the computing device 202 may be configured to access the three-dimensional model and compare the determined real-world location of the probe tip 104 within the gas turbine engine 10 to the computer-based model so as to identify a corresponding virtual location of the probe tip 104 within the model. The three-dimensional model may then be presented to a user of the system 200 with the virtual location of the probe tip 104 being displayed as a symbol or other visual indicator (e.g., a dot, star, "X" or any other suitable identifying mark) within the model.

Figure 6:
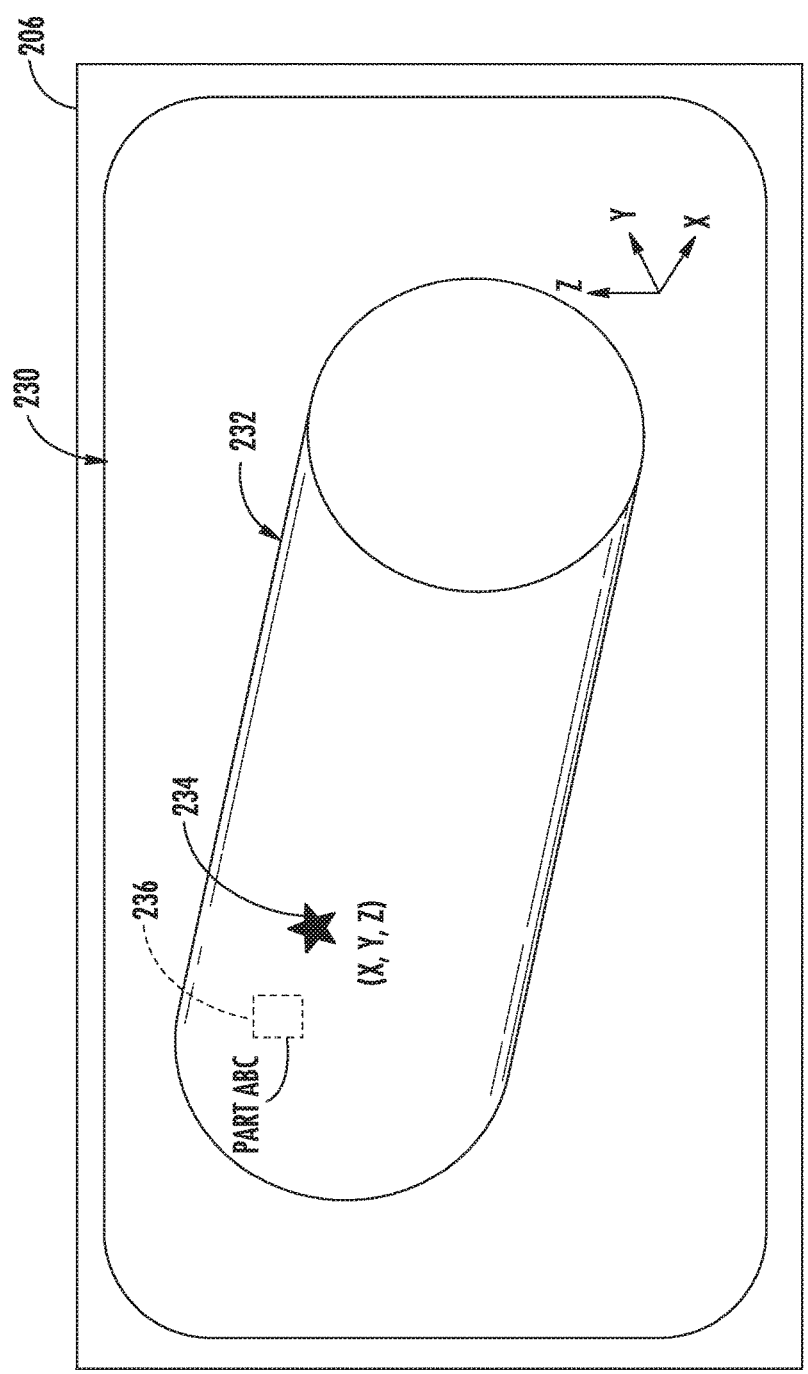
FIG. 6 illustrates a simplified view of a user interface that may be presented to a user of the disclosed system in accordance with aspects of the present subject matter, particularly illustrating a visual indicator being used to represent a virtual location of a probe within a three-dimensional model of a gas turbine engine that corresponds to the current real-world location of the probe within the engine.

For example, FIG. 6 illustrates a simplified view of a user interface 230 that may be presented to a user of the system 200. As shown, the three-dimensional model of the gas turbine 10 (indicated schematically as cylinder 232 in FIG. 6) may be presented on the display device 206. In addition, a visual indicator 234 may be displayed within the three-dimensional model 232 that represents the current location of the probe tip 104 within the engine 10. As such, by manipulating the three-dimensional model 232 (e.g., by zooming the model 232 in or out, by rotating the model 232, by making one or more of the modeled components of the engine transparent and/or the like), a user of the system 200 may be allowed to view the exact location of the probe tip 104 relative to one or more internal components of the engine 10, such as one or more compressor blades 82 or turbine blades 68 of the engine 10. The user may then manipulate the real-world location of the probe tip 104 within the engine 10, as is necessary or desired, based on the virtual location displayed within the model 232 to precisely position the probe tip 104 relative to the internal component(s) of the engine 10.

It should be appreciated that the virtual location of the probe tip 104 displayed within the three-dimensional model may be continuously updated as the real-world location of the probe tip 104 is adjusted within the gas turbine engine 10. For example, as the user manipulates the actual location of the probe tip 104 within the engine 10, an updated location for the probe tip 104 may be determined by the computing device 202. The virtual location within the three-dimensional model may then be adjusted based on the updated location of the probe tip 104, thereby providing the user with a real-time virtual representation of the current location of the probe tip 104.

It should also be appreciated that, in addition to the virtual location of the probe tip 104, the computing device 202 may also be configured to display the name(s), part number(s) and/or other identifying information related to the internal engine component(s) disposed adjacent to the probe tip 104. For instance, as shown in FIG. 6, identifying information associated with an adjacent engine component(s) 236 may be presented within the user interface that is being displayed to the user of the system 200 via the display device 206.

Additionally, it should be appreciated that, although the computing device 202 and the display device 206 are shown as separate components within the system 200, such components may be integrated into or otherwise form part of the probe 100. For instance, in one embodiment, the computing device 202 and associated display 206 may be built into the probe 100 as an integrated assembly.

Figure 7:
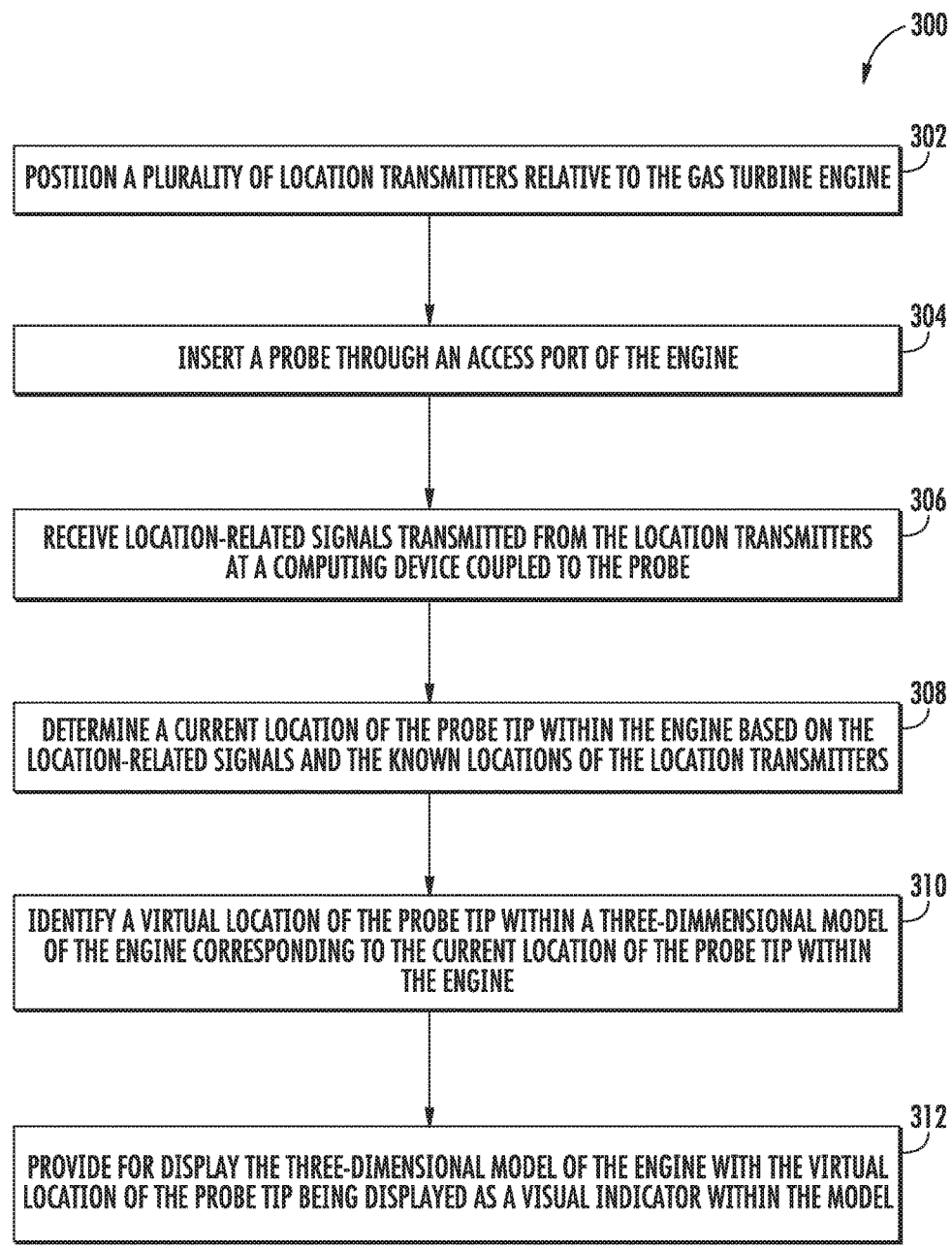
FIG. 7 illustrates a flow diagram of one embodiment of a method for locating a probe within a gas turbine engine in accordance with aspects of the present subject matter.

Referring now to FIG. 7, a flow diagram of one embodiment of a method 300 for locating a probe within a gas turbine engine is illustrated in accordance with aspects of the present subject matter. In general, the method 300 will be discussed herein with reference to the gas turbine engine 10 and the system 200 described above with reference to FIGS. 1-6. However, it should be appreciated by those of ordinary skill in the art that the disclosed method 300 may generally be implemented with gas turbine engines having any other suitable engine configuration and/or with systems having any other suitable system configuration. In addition, although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 7, at (302), the method 300 may include positioning a plurality of location transmitters relative to the gas turbine. For example, as indicated above, each location transmitter 204 may, in one embodiment, be installed or positioned within an access port 62 of the engine 10. Alternatively, the location transmitters 204 may be positioned at any other suitable location relative to the engine 10 that allows for the transmitters 204 to function as described herein.

Additionally, at (304), the method 300 may include inserting a probe through an access port of the engine. For example, as indicated above, the probe 100 may be inserted through one of the access ports 62 of the engine 10 to allow internal views or images to be obtained for visually inspecting the interior of the engine 10. In addition, once inserted within the interior of the engine 10, the probe 100 may be configured to receive the location-related signals transmitted by the various location transmitters 204 (e.g., via the probe's location signal receiver 120). The location-related signals may then, at (306), be transmitted to and received at a computing device coupled to the probe. For example, as indicated above, the probe 100 may be communicatively coupled to a computing device 202 to allow both the internal images obtained by the probe 100 and the location-related signals received by the probe 100 to be transmitted to the computing device 202.

Moreover, at (308), the method 300 may include determining a current location of the probe tip within the engine based on the location-related signals and the known locations of the location transmitters. For example, in one embodiment, the computing device 202 may be configured to utilize the location-related signals to calculate a distance defined between the probe tip 104 and each the location transmitter 204. The calculated distances along with the known locations of the location transmitters 204 may then be used to implement a trilateration technique to determine the current location of the probe tip 104 with the engine 10.

In other embodiments, the computing device 202 may be configured to utilize the location-related signals to calculate an angle defined between the probe tip 104 and each the location transmitter 204. The calculated angles along with the known locations of the location transmitters 204 may then be used to implement a triangulation technique to determine the current location of the probe tip 104 with the engine 10.

Referring still to FIG. 7, at (310), the method 300 may include identifying a virtual location of the probe tip within a three-dimensional model of the engine corresponding to the current location of the probe tip within the engine. For example, as indicated above, the computing device 202 may be configured to correlate the real-world location of the probe tip 104 within the engine 10 to a corresponding virtual location within the model of the engine 10. Thereafter, at (312), the computing device 202 may be configured to provide the three-dimensional model for display with the virtual location of the probe tip 104 being displayed or represented as a visual indicator within the model. For instance, as indicated above, the computing device 202 may be configured to transmit the model to an associated display device 206 for presentation to a user of the system 200.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for locating probes within a gas turbine engine, the method comprising:
    positioning a plurality of location transmitters relative to the gas turbine engine, each location transmitter of the plurality of location transmitters having a known location relative to the gas turbine engine;
    inserting a probe through an access port of the gas turbine engine, the probe including a probe tip and a location signal receiver, the location signal receiver being configured to receive location-related signals transmitted from the plurality of location transmitters, and wherein the probe is configured to perform a procedure on an internal engine component of the gas turbine engine;
    wherein positioning the plurality of location transmitters relative to the gas turbine engine comprises positioning the plurality of location transmitters within a plurality of access ports of the gas turbine engine, the plurality of access ports differing from the access port through which the probe is inserted;
    receiving the location-related signals at a computing device communicatively coupled to the probe;
    determining, by the computing device, a current location of the probe tip within the gas turbine engine based on the location-related signals and the known locations of the plurality of location transmitters;
    identifying, with the computing device, a virtual location of the probe tip within a three-dimensional model of the gas turbine engine corresponding to the current location of the probe tip within the gas turbine engine; and
    providing for display, by the computing device, the three-dimensional model of the gas turbine engine, wherein the virtual location of the probe tip is displayed as a visual indicator within the three-dimensional model.

2. The method of claim 1, wherein positioning the plurality of location transmitters relative to the gas turbine engine comprises positioning at least three location transmitters relative to the gas turbine engine.

3. The method of claim 1, wherein determining the current location of the probe tip within the gas turbine engine comprises determining a distance defined between the probe tip and each location transmitter of the plurality of location transmitters based on the location-related signals.

4. The method of claim 3, wherein determining the current location of the probe tip within the gas turbine engine further comprises determining the current location of the probe tip within the gas turbine using a trilateration technique based on the distances defined between the probe tip and the plurality of location transmitters and the known locations of the plurality of location transmitters.

5. The method of claim 1, wherein determining the current location of the probe tip within the gas turbine engine comprises determining a respective angle defined between the probe tip and each location transmitter of the plurality of location transmitters based on the location-related signals.

6. The method of claim 5, wherein determining the current location of the probe tip within the gas turbine engine further comprises determining the current location of the probe tip within the gas turbine using a triangulation technique based on the respective angles defined between the probe tip and the plurality of location transmitters and the known locations of the plurality of location transmitters.

7. The method of claim 1, further comprising:
    moving the probe within the gas turbine engine; and
    determining, by the computing device, an updated location of the probe tip within the gas turbine engine.

8. The method of claim 7, further comprising adjusting, by the computing device, a position of the visual indicator within the three-dimensional model of the gas turbine engine based on the updated location of the probe tip.

9. The method of claim 1, wherein the probe corresponds to one of a borescope, a videoscope or a fiberscope.

10. The method of claim 1, wherein the probe includes a light source for illuminating an interior of the gas turbine engine.

11. The method of claim 1, wherein the procedure comprises repairing cracks on the internal engine component of the gas turbine engine.

12. The method of claim 1, further comprising receiving, with the computing device, image data associated with a plurality of images obtained by the probe of an interior of the gas turbine engine.

13. The method of claim 12, wherein the image data is configured to be inspected to identify any defects or damage within the gas turbine engine.

14. The method of claim 12, wherein providing for display the three-dimensional model of the gas turbine engine comprises providing for display both the three-dimensional model of the gas turbine engine and the image data obtained from the probe.

15. A method for locating optical probes within a gas turbine engine, the method comprising:
    positioning a plurality of location transmitters relative to the gas turbine engine, each location transmitter of the plurality of location transmitters having a known location relative to the gas turbine engine;
    inserting an optical probe through an access port of the gas turbine engine, the optical probe including a probe tip and a location signal receiver, the location signal receiver being configured to receive location-related signals transmitted from the plurality of location transmitters, and wherein the optical probe is configured to perform a procedure on an internal engine component of the gas turbine engine;

wherein positioning the plurality of location transmitters relative to the gas turbine engine comprises positioning the plurality of location transmitters within a plurality of access ports of the gas turbine engine, the plurality of access ports differing from the access port through which the optical probe is inserted;

receiving the location-related signals at a computing device communicatively coupled to the optical probe;

receiving, with the computing device, image data associated with a plurality of images obtained by the optical probe of an interior of the gas turbine engine;

determining, by the computing device, a current location of the probe tip within the gas turbine engine based on the location-related signals and the known locations of the plurality of location transmitters;

identifying, with the computing device, a virtual location of the probe tip within a three-dimensional model of the gas turbine engine corresponding to the current location of the probe tip within the gas turbine engine; and providing for display, by the computing device, the three-dimensional model of the gas turbine engine, wherein the virtual location of the probe tip is displayed as a visual indicator within the three-dimensional model.

16. The method of claim 15, further comprising:

moving the optical probe within the gas turbine engine; and determining, by the computing device, an updated location of the probe tip within the gas turbine engine.

17. The method of claim 16, further comprising adjusting, by the computing device, a position of the visual indicator within the three-dimensional model of the gas turbine engine based on the updated location of the probe tip.

18. The method of claim 15, wherein the optical probe corresponds to one of a borescope, a videoscope or a fiberscope.

19. The method of claim 15, wherein providing for display the three-dimensional model of the gas turbine engine comprises providing for display both the three-dimensional model of the gas turbine engine and the image data obtained from the optical probe.

\* \* \* \* \*